(12) United States Patent
Rées

(10) Patent No.: US 6,250,313 B1
(45) Date of Patent: Jun. 26, 2001

(54) TEETH-CLEANSING MEANS

(76) Inventor: Anne du Rées, Tulevägen 20A, SE-181 41 Lidingö (SE)

( * ) Notice: Subject to any disclaimer, the term of this patent is extended or adjusted under 35 U.S.C. 154(b) by 0 days.

(21) Appl. No.: 09/446,993

(22) PCT Filed: Jul. 3, 1998

(86) PCT No.: PCT/SE98/01320

§ 371 Date: Dec. 30, 1999

§ 102(e) Date: Dec. 30, 1999

(87) PCT Pub. No.: WO99/01082

PCT Pub. Date: Jan. 14, 1999

(30) Foreign Application Priority Data

Jul. 4, 1997 (SE) .................................................. 9702594

(51) Int. Cl.⁷ .................................................. A61C 15/04
(52) U.S. Cl. ........................................ 132/321; 132/329
(58) Field of Search .................................. 132/321, 323, 132/325

(56) References Cited

U.S. PATENT DOCUMENTS

| | | | |
|---|---|---|---|
| 1,069,874 | * | 8/1913 | Hanscom . |
| 3,789,858 | * | 2/1974 | Pesce . |
| 4,008,727 | * | 2/1977 | Thornton . |
| 4,142,538 | * | 3/1979 | Thornton . |
| 4,265,258 | | 5/1981 | Eaton, II . |
| 4,277,297 | * | 7/1981 | Thorton . |
| 4,974,615 | * | 12/1990 | Doundoulkis .......................... 132/321 |
| 5,063,948 | * | 11/1991 | Lloyd .................................... 132/321 |
| 5,315,028 | | 5/1994 | Wu . |
| 5,316,028 | * | 5/1994 | Flemming ............................. 132/329 |
| 5,505,216 | * | 4/1996 | Gilligan ................................ 132/321 |
| 5,545,480 | * | 8/1996 | Lalani .................................... 428/364 |
| 5,560,377 | | 10/1996 | Donovan . |
| 5,682,911 | * | 11/1997 | Harada .................................. 132/321 |
| 5,878,758 | * | 3/1999 | Bacino et al. ........................ 132/321 |
| 6,112,753 | * | 9/2000 | Arsenault ............................. 132/323 |

FOREIGN PATENT DOCUMENTS 9220255   11/1992   (WO) .

* cited by examiner

Primary Examiner—Ralph A. Lewis
(74) Attorney, Agent, or Firm—Ostrolenk, Faber, Gerb & Soffen, LLP

(57) ABSTRACT

A teeth cleaning device including an elongated length of dental floss which has brush formations at spaced intervals therealong with a greater cross section than that of the floss. The brush formation is retained on the dental floss by heating the brush formation to be melted to the floss and, in particular, by forming the floss from a core wire and a meltable melt wire which is heated to melt the melt wire to hold the brush formation to the floss.

12 Claims, 2 Drawing Sheets

TEETH-CLEANSING MEANS

BACKGROUND OF THE INVENTION

The present invention relates to a dental cleaning device in the shape of an elongated element, the cross-section of which permits its introduction between the teeth.

In order to avoid parodontopati and caries it is important regularly to clean the teeth and to give them a prophylactic care at all stages. To achieve this one does today generally use a dental floss and, when the gaps between the teeth are a little wider, use so-called gap brushes. It has, however, proven difficult to achieve a perfect cleaning of the teeth in those cases where the dental floss is too thin and the gap brush is too big. If the gap brush is too big to permit its introduction, it will bend resulting in a deteriorated cleaning effect. If in such a case the dental floss is inserted between the teeth, the cleaning effect will be inferior due to the fact that in those places the dental floss is too thin to perform the desired result.

SUMMARY OF THE INVENTION

The purpose of the present invention is to eliminate the above-mentioned problem and to establish a combined dental floss and gap brush, the two parts of which cooperate in such a way that a most efficient and complete cleaning of the teeth can take place. The characteristics of the invention are set out in the subsequent claims.

Thanks to the present invention there has now been provided a tooth cleaning device, which in an excellent manner fulfils its purposes and at the same time can be manufactured in a simple and cost-saving way. Use of the tooth cleaning device according to the invention makes it possible simultaneously to handle two problems, namely alternately caries and parodontal problems. The device offers a more efficient cleaning than a conventional gap brush, when the brush is inserted with the aid of the dental floss and can be given different angles during the cleaning of the gum. In this way the lingual side of the gum becomes more healthy, which significantly improves the parodontal situation. Also, thanks to the alternate use of the gap brush and the dental floss, the device according to the invention offers a possibility simultaneously to carry out two treatments. Use of the dental floss makes it possible also to reach very narrow spaces between the teeth, which cannot accommodate a conventional gap brush so that efficient cleaning can be carried out. Further, one can conveniently reach the spaces below bridge structures at implants and pending joints. Finally, the dimensions of both the brush and the dental floss can conveniently be made to match individual users and the device can be delivered to the client e.g. wound onto a roll. The application of the brush on the dental floss according to the method characterizing the invention completely eliminates the risk that the brush would come loose from the dental floss. This is essential, since the brush may in use sometimes get stuck between the teeth.

BRIEF DESCRIPTION OF THE DRAWINGS

A preferred embodiment of the invention will now be described with reference to the drawings, in which FIG. 1 diagrammatically illustrates the manufacturing process for a dental floss according to the invention

DESCRIPTION OF THE PREFERRED EMBODIMENT

Figure 2:
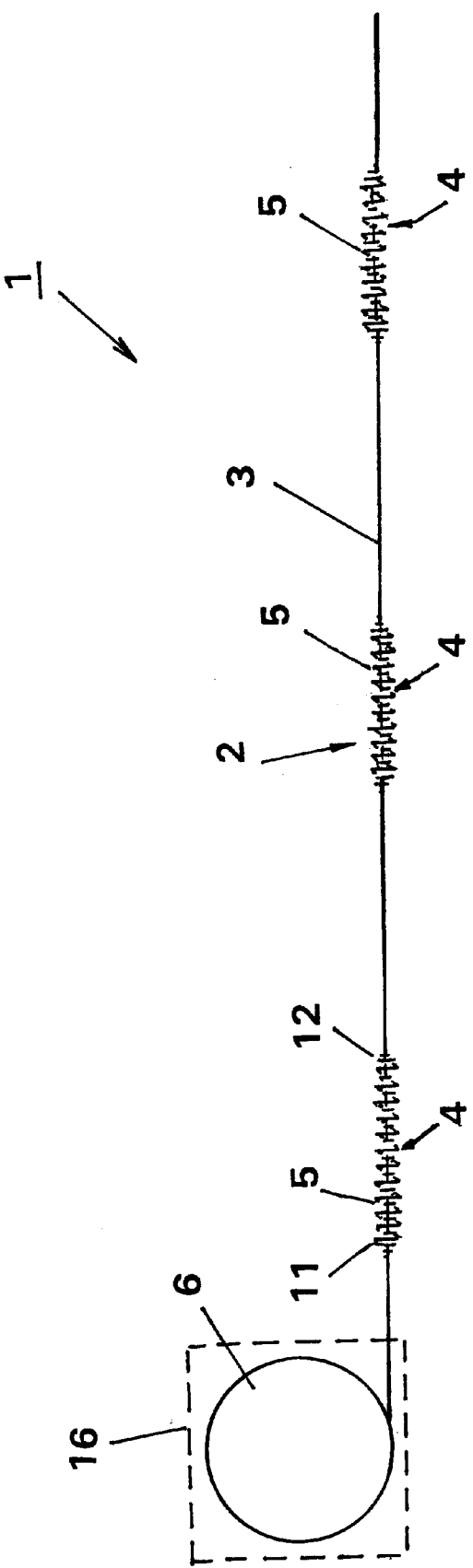
FIG. 2 shows a tooth cleaning device according to the invention, which has been pulled out a predetermined length from a storage roll.

As appears from FIG. 2, the tooth cleaning device 1 is constituted by an elongated element 2, the cross-sectional dimension of which permits its introduction between the teeth. The elongated element is constituted by a dental floss 3, which as seen in its longitudinal direction exhibits a number of brush formations 4 spaced from each other in a predetermined way. The cross-sectional dimension of the brush formations is greater than that of the dental floss 3.

In the illustrated embodiment the brush formations 4 comprise a bristle 5 projecting laterally by a distance matching the distance to the teeth to be cleaned. In order to facilitate the insertion of the bristle 5 between the teeth each brush formation 4 is bevelled at least at the one of its ends 11 or 12, respectively. The brush formations are also located at a regular spacing from each other which may vary but, in the illustrated example, amounts to about 30 cms. The length of each individual brush formation can be about 1–5 cms and in the illustrated example the cylinder-shaped portion of each brush formation has a diameter of approximately 2–5 mms.

The brush formations 4 are in some suitable way retained in their positions along the dental floss 3. In the example shown the brush formations 4 have been fixed at the dental floss 3 by being twined into it or by means of heating, e.g. pulse heating including use of a melt wire 8. According to the illustrated example the melt wire 8 has substantially the same melting point as that of the bristle 5. In those cases when the melt wire 8 is used the dental floss 3 does in addition to the melt wire 8 just mentioned also comprise a core wire 7, the melting point of which is higher than that of the melt wire. Suitable materials in this context are polymers, which may include up to 100 strands in each wire 7 and 8, respectively, and also in the individual bristle 5. Before the application of the brush formations 4 these may either be parallel to each other or intertwined.

Figure 1:
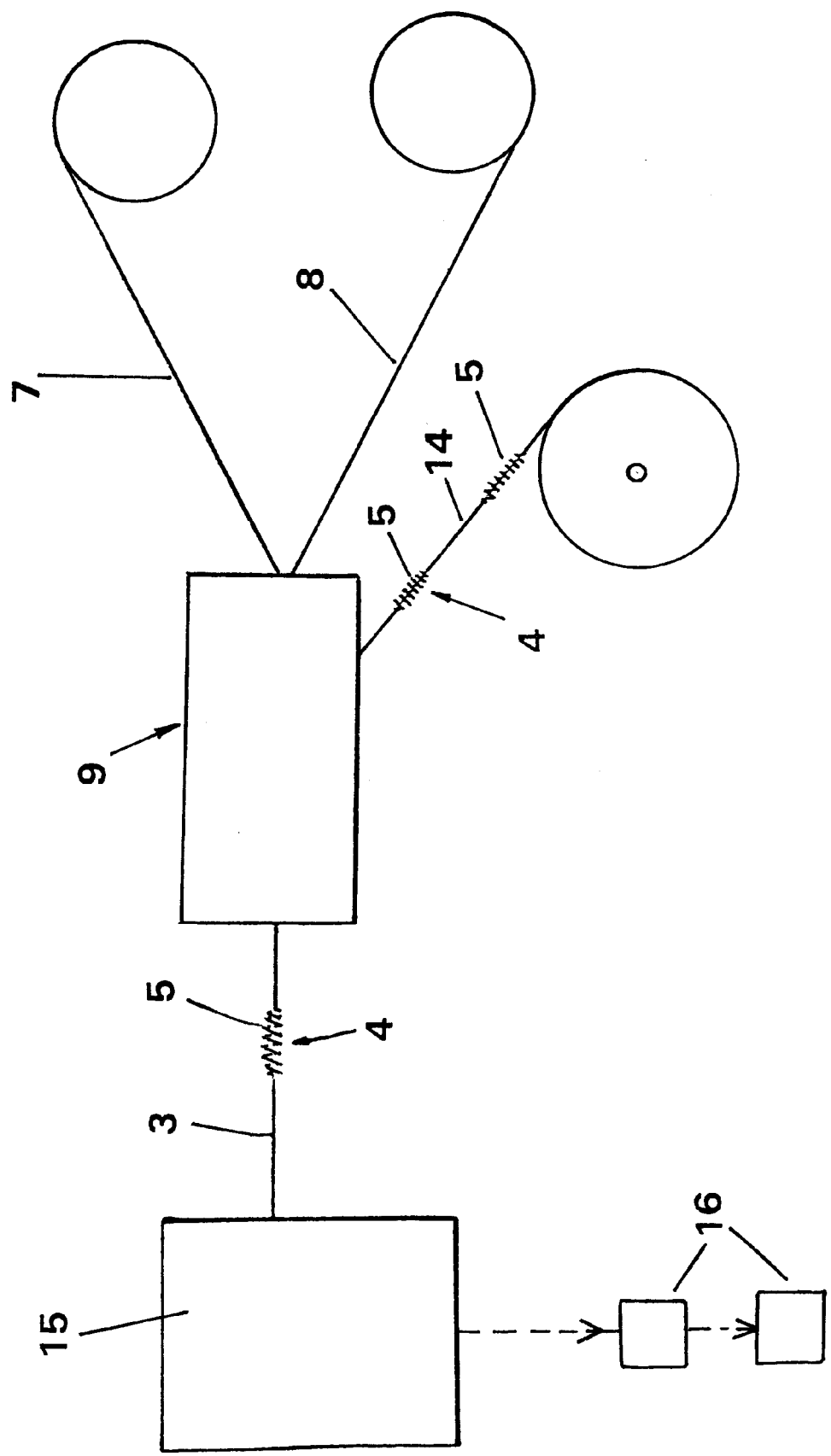

As appears more in detail from FIG. 1, it has there diagrammatically been shown how the core wire 7 and the melt wire 8 are supplied to a brush application station 9, the brush formations 4 being simultaneously by means of a carrier wire 14 fed into the station 9, where heating pulses secure the bristle to the dental floss 3. During that operation the melt wire 8, which has substantially the same melting point as the bristle 5 in the brush formations 4, will by melting secure those to the core wire 7, whereupon the completed dental floss 3 is supplied to a cutting and packaging station 15. Thanks to the fact that the core wire 7 has a higher melting point than have both the bristle 5 and the melt wire 8, it can be preserved intact during the pulse heating in the brush application station 9.

In the example shown the tooth cleaning device 1 has been wound on a roll 6, which in turn can be enclosed in suitably designed packages 16. Those packages 16 may contain tooth cleaning devices including brushes and dental flosses of different dimensions or sizes to suit a maximum number of users.

The mode of operation of the device 1 according to the invention is as follows. A suitable length of the dental floss 3 having brush formations 4 is pulled out from the storage roll 6. The dental floss 3 may or may not then be cut loose from the roll and inserted into the gap between two teeth to be cleaned. With the aid of the floss it is then easy to make the brush formations 4 enter that gap, which could not accommodate a gap brush in a way permitting cleaning. Also, one can conveniently vary the angle of the bristle 5 so that the teeth are cleaned in a most efficient way. When the space in question has been cleaned, the device 1 is pulled back so that the dental floss only remains in the gap, whereupon the device 1 is withdrawn. All tooth gaps are then cleaned in the same manner. In those cases where the gaps between the teeth are very narrow,. only the portion of the device 1 comprising the dental floss 3 is made use of.

What is claimed is:

1. A dental cleaning device comprising an elongate dental floss, at least one brush formation of greater cross section than the dental floss but of shorter length than the dental floss positioned along the length of the dental floss;

meltable material at the dental floss, and the brush formations being held to the dental floss by the meltable material.

2. The dental cleaning device of claim 1, wherein the meltable material has substantially the same melting point as the brush formation.

3. The dental cleaning device of claim 1, wherein the dental floss is comprised of a core wire and a melt wire which are held together; and the melt wire being the meltable material and being melted to hold the brush formation to the floss.

4. The dental cleaning device of claim 3, wherein the melt wire has a melting point lower than the core wire such that melting of the melt wire sufficiently to hold the brush formation does not melt the core wire.

5. The dental cleaning device of claim 4, wherein the brush formation has substantially the same melting point as the melt wire.

6. The dental cleaning device of claim 5, wherein the core wire, the melt wire and the brush formation are in fixed positions relative to each other and are brought into the fixed positions by means of pulse heating thereof.

7. The dental cleaning device of claim 4, wherein the core wire, the melt wire and the brush formation all are comprised of polymers.

8. The dental cleaning device of claim 1, wherein there are a plurality of the brush formations at spaced intervals along the dental floss.

9. The dental cleaning device of claim 1, wherein the brush formation has opposite ends and at least one of the ends is tapered for facilitating insertion between a user's teeth.

10. A method for manufacturing an elongated tooth cleaning device which includes a length of dental floss and at least one brush formation along the length of dental floss, wherein the brush formation has a greater cross section than the dental floss, the method comprising:

forming dental floss from at least a core wire and a meltable wire, bringing a brush formation to the floss and applying the brush formation to the dental floss by heating for melting the meltable wire to hold the brush formation to the floss.

11. The method of claim 10, further comprising bringing a plurality of the brush formations to the floss and applying the brush formations to the floss at spaced intervals.

12. The method of claim 11, further comprising subsequently cutting lengths of the dental floss each with a respective one of the brush formations and packaging a length of the dental floss.

* * * * *